(12) United States Patent
Rand et al.

(10) Patent No.: US 8,245,704 B2
(45) Date of Patent: *Aug. 21, 2012

(54) DISPENSER WITH DOSES' COUNTER

(75) Inventors: Paul Kenneth Rand, Redhill (GB); Peter John Brand, Royston (GB); James William Godfrey, Hertfordshire (GB)

(73) Assignee: Glaxo Group Limited, Greenford, Middlesex (GB)

( * ) Notice: Subject to any disclaimer, the term of this patent is extended or adjusted under 35 U.S.C. 154(b) by 965 days.

This patent is subject to a terminal disclaimer.

(21) Appl. No.: 11/459,048

(22) Filed: Jul. 21, 2006

(65) Prior Publication Data

US 2006/0289008 A1      Dec. 28, 2006

Related U.S. Application Data

(63) Continuation of application No. 10/465,109, filed on Jun. 19, 2003, now Pat. No. 7,107,986, which is a continuation of application No. 10/224,000, filed on Aug. 20, 2002, now Pat. No. 6,601,582, which is a continuation of application No. 09/445,658, filed as application No. PCT/EP98/03379 on Jun. 8, 1998, now Pat. No. 6,474,331.

(30) Foreign Application Priority Data

Jun. 10, 1997 (GB) .................................. 9711889.7
Oct. 16, 1997 (GB) .................................. 9721875.4

(51) Int. Cl.
*A61M 11/00* (2006.01)
*A61M 15/00* (2006.01)
*A61M 16/00* (2006.01)

(52) U.S. Cl. ......... 128/200.23; 128/200.24; 128/200.14; 128/203.15; 128/203.12

(58) Field of Classification Search ............. 128/203.14, 128/203.15, 205.23, 200.11–200.24, 203.12; 222/36, 38, 48, 162, 32, 33, 402, 402.11, 222/402.13, 13; 116/285, 311, 312, 315, 116/308, 318; 604/58; 215/230; 206/459.1, 206/459.5
See application file for complete search history.

(56) References Cited

U.S. PATENT DOCUMENTS 3,119,557 A      1/1964    Chapman
(Continued)

FOREIGN PATENT DOCUMENTS

DE         1954623         5/1971
(Continued)

OTHER PUBLICATIONS

U.S. Appl. No. 09/445,673—Office Action issued Feb. 15, 2001.
(Continued)

*Primary Examiner* — Annette Dixon
(74) *Attorney, Agent, or Firm* — James P. Riek (57) ABSTRACT

There is provided a dispenser suitable for dispensing medicament, particularly medicament for use in the treatment of respiratory disorders. The dispenser comprises a housing having a support; a container, locatable within said housing, having an outlet, wherein said container dispenses through said outlet in response to movement of the container relative to the housing; and an actuation indicator having an indexing mechanism actuatable by movement of the container relative to the housing. A couple mechanism is provided which couples the indexing mechanism to the container to compensate for any variation in pre-actuation positionings of the indexing mechanism and container.

7 Claims, 7 Drawing Sheets

U.S. PATENT DOCUMENTS

| | | |
|---|---|---|
| 3,411,368 A | 11/1968 | Schneiter |
| 3,722,461 A * | 3/1973 | Forman .................... 116/223 |
| 3,822,808 A * | 7/1974 | Katakura et al. ............... 222/33 |
| 4,037,719 A * | 7/1977 | Perlmutter ................. 206/266 |
| 4,196,985 A | 4/1980 | Kratt |
| 4,311,050 A | 1/1982 | Bessman |
| 4,495,944 A | 1/1985 | Brisson et al. |
| 4,499,370 A | 2/1985 | Nishiuchi |
| 4,506,373 A | 3/1985 | Kratt |
| 4,565,302 A | 1/1986 | Pfeiffer et al. |
| 4,805,811 A | 2/1989 | Wetterlin |
| 4,809,692 A | 3/1989 | Nowacki et al. |
| 4,817,822 A | 4/1989 | Rand et al. |
| 4,934,358 A | 6/1990 | Nilsson et al. |
| 4,937,798 A | 6/1990 | Zepf |
| 4,955,371 A | 9/1990 | Zamba et al. |
| 4,973,867 A | 11/1990 | Sudler |
| 5,009,338 A | 4/1991 | Barker |
| 5,017,542 A | 5/1991 | Martan et al. |
| 5,020,527 A | 6/1991 | Dessertine |
| 5,042,467 A | 8/1991 | Foley |
| 5,069,204 A | 12/1991 | Smith et al. |
| 5,148,355 A | 9/1992 | Lowe et al. |
| 5,209,375 A | 5/1993 | Fuchs |
| 5,228,586 A * | 7/1993 | Fuchs ............................ 222/38 |
| 5,242,067 A | 9/1993 | Garby et al. |
| 5,242,405 A | 9/1993 | Howe |
| 5,259,499 A | 11/1993 | Boettger |
| 5,261,548 A | 11/1993 | Barker et al. |
| 5,263,475 A | 11/1993 | Altermatt et al. |
| 5,279,422 A | 1/1994 | Adams |
| 5,289,946 A | 3/1994 | Fuchs |
| 5,300,042 A | 4/1994 | Kossoff et al. |
| 5,349,945 A | 9/1994 | Wass et al. |
| 5,358,117 A | 10/1994 | Adams |
| 5,363,842 A | 11/1994 | Mishelevich et al. |
| 5,411,173 A | 5/1995 | Weinstein |
| 5,458,135 A | 10/1995 | Patton et al. |
| 5,464,970 A | 11/1995 | Nill et al. |
| 5,482,030 A * | 1/1996 | Klein ..................... 128/200.23 |
| 5,505,192 A | 4/1996 | Samiotes et al. |
| 5,522,378 A | 6/1996 | Ritson et al. |
| 5,544,647 A | 8/1996 | Jewett et al. |
| 5,564,414 A * | 10/1996 | Walker et al. ............ 128/200.23 |
| 5,622,163 A | 4/1997 | Jewett et al. |
| 5,625,659 A | 4/1997 | Sears |
| 5,657,748 A | 8/1997 | Braithwaite |
| 5,718,355 A | 2/1998 | Garby et al. |
| 5,772,074 A | 6/1998 | Dial et al. |
| 5,794,612 A | 8/1998 | Wachter et al. |
| 5,809,997 A | 9/1998 | Wolf |
| 5,826,571 A | 10/1998 | Casper et al. |
| 5,829,434 A * | 11/1998 | Ambrosio et al. ....... 128/203.15 |
| 5,871,007 A | 2/1999 | Clark |
| 5,988,496 A | 11/1999 | Bruna |
| 6,012,450 A | 1/2000 | Rubsamen |
| 6,029,659 A | 2/2000 | O'Connor |
| 6,076,521 A | 6/2000 | Lindahl et al. |
| 6,082,358 A | 7/2000 | Scarrott et al. |
| 6,119,684 A | 9/2000 | Nohl et al. |
| 6,131,566 A | 10/2000 | Ashurst et al. |
| 6,138,669 A | 10/2000 | Rocci et al. |
| 6,142,339 A * | 11/2000 | Blacker et al. .................. 222/23 |
| 6,149,054 A | 11/2000 | Cirrillo et al. |
| 6,161,724 A | 12/2000 | Blacker et al. |
| D439,534 S | 3/2001 | Scarrott et al. |
| 6,202,642 B1 | 3/2001 | McKinnon et al. |
| 6,223,744 B1 | 5/2001 | Garon |
| 6,234,168 B1 | 5/2001 | Bruna |
| 6,260,549 B1 | 7/2001 | Sosiak |
| D447,432 S | 9/2001 | Scarrott et al. |
| 6,328,037 B1 | 12/2001 | Scarrott et al. |
| 6,336,453 B1 | 1/2002 | Scarrott et al. |
| 6,360,739 B1 * | 3/2002 | Rand et al. ............... 128/200.23 |
| D456,292 S | 4/2002 | Scarrott et al. |
| 6,425,392 B1 | 7/2002 | Sosiak |
| 6,431,168 B1 * | 8/2002 | Rand et al. ............... 128/200.23 |
| 6,435,372 B1 | 8/2002 | Blacker et al. |
| 6,474,331 B1 * | 11/2002 | Rand et al. ............... 128/200.23 |
| 6,516,799 B1 | 2/2003 | Greenwood et al. |
| 6,561,384 B2 | 5/2003 | Blacker et al. |
| 6,565,743 B1 | 5/2003 | Poirier et al. |
| 6,601,582 B2 | 8/2003 | Rand et al. |
| 6,659,307 B1 | 12/2003 | Stradella |
| 6,729,330 B2 | 5/2004 | Scarrott et al. |
| 6,761,161 B2 | 7/2004 | Scarrott et al. |
| 6,926,002 B2 | 8/2005 | Scarrott et al. |
| 6,938,798 B2 | 9/2005 | Stradella et al. |
| 6,953,039 B2 | 10/2005 | Scarrott et al. |
| 7,107,986 B2 * | 9/2006 | Rand et al. ............... 128/200.23 |
| 7,500,444 B2 * | 3/2009 | Bonney et al. ................. 116/311 |
| 7,832,351 B2 * | 11/2010 | Bonney et al. ................. 116/311 |
| 7,984,826 B2 * | 7/2011 | Blacker et al. .................. 222/36 |
| 2004/0222237 A1 | 11/2004 | Blacker et al. |

FOREIGN PATENT DOCUMENTS

| | | |
|---|---|---|
| DE | 3047491 | 7/1982 |
| DE | 3405352 | 8/1985 |
| DE | 8602238 U | 4/1986 |
| DE | G 86 02 238.5 | 5/1986 |
| EP | 0078787 | 5/1983 |
| EP | 0111163 | 6/1984 |
| EP | 0 178 925 | 4/1986 |
| EP | 0 196 581 | 10/1986 |
| EP | 0 220 132 | 4/1987 |
| EP | 0 227 022 | 7/1987 |
| EP | 0 254 391 | 1/1988 |
| EP | 0 269 496 | 6/1988 |
| EP | 0 280 104 | 8/1988 |
| EP | 0 327 910 | 8/1989 |
| EP | 0 387 222 | 9/1990 |
| EP | 0 448 204 | 9/1991 |
| EP | 0 450 905 | 10/1991 |
| EP | 0 480 488 | 4/1992 |
| EP | 0 525 476 | 2/1993 |
| EP | 0 543 156 | 5/1993 |
| EP | 0 636 421 | 2/1995 |
| EP | 0 684 047 | 11/1995 |
| EP | 0 688 572 | 12/1995 |
| EP | 0 988 077 | 8/1998 |
| EP | 1 163 922 | 8/1998 |
| EP | 0 986 412 | 3/2000 |
| FR | 2 428 286 | 1/1980 |
| GB | 893717 | 4/1962 |
| GB | 1101514 | 1/1968 |
| GB | 1136886 | 12/1968 |
| GB | 1204589 | 9/1970 |
| GB | 1296484 | 11/1972 |
| GB | 1317315 | 5/1973 |
| GB | 1392945 | 5/1975 |
| GB | 2002120 | 2/1979 |
| GB | 2012963 | 8/1979 |
| GB | 2024477 | 1/1980 |
| GB | 2024478 | 1/1980 |
| GB | 1568808 | 6/1980 |
| GB | 2063075 | 6/1981 |
| GB | 2114790 | 8/1983 |
| GB | 2145699 | 4/1985 |
| GB | 2153445 | 8/1985 |
| GB | 2156783 | 10/1985 |
| GB | 2164569 | 3/1986 |
| GB | 2170780 | 8/1986 |
| GB | 2191032 | 12/1987 |
| GB | 2191326 | 12/1987 |
| GB | 2195544 | 4/1988 |
| GB | 2199308 | 7/1988 |
| GB | 2262452 | 6/1993 |
| GB | 2263068 | 7/1993 |
| GB | 2265142 | 9/1993 |
| JP | 5-361 | 8/1993 |
| JP | 6-26891 | 2/1994 |
| JP | 9-250059 | 9/1997 |
| WO | 85 02765 | 7/1985 |
| WO | 86 02275 | 4/1986 |
| WO | 86 05991 | 10/1986 |
| WO | 87 04354 | 7/1987 |
| WO | 90 02576 | 3/1990 |

| | | |
|---|---|---|
| WO | 90 13327 | 11/1990 |
| WO | 91 06334 | 5/1991 |
| WO | 92 00771 | 1/1992 |
| WO | 92 17231 | 10/1992 |
| WO | 9217231 A1 | 10/1992 |
| WO | 93 07922 | 4/1993 |
| WO | 93 09324 | 5/1993 |
| WO | 93 11813 | 6/1993 |
| WO | 93 12823 | 7/1993 |
| WO | 93 21980 | 11/1993 |
| WO | 93 24167 | 12/1993 |
| WO | 94 10544 | 5/1994 |
| WO | 94 11272 | 5/1994 |
| WO | 94 14492 | 7/1994 |
| WO | 95 07723 | 3/1995 |
| WO | 95 07724 | 3/1995 |
| WO | 95 16483 | 6/1995 |
| WO | 95 22365 | 8/1995 |
| WO | 95 26769 | 10/1995 |
| WO | 95 34874 | 12/1995 |
| WO | 96 16686 | 6/1996 |
| WO | 96 39337 | 12/1996 |
| WO | 98 56444 | 12/1998 |
| WO | 98 56445 | 12/1998 |
| WO | 98 56446 | 12/1998 |
| WO | 99 36115 | 7/1999 |

OTHER PUBLICATIONS

U.S. Appl. No. 10/465,109—Office Action issued Oct. 15, 2003.
U.S. Appl. No. 10/465,109—Office Action issued Jun. 14, 2005.

* cited by examiner

FIG. 1

(PRIOR ART)

DISPENSER WITH DOSES' COUNTER

CROSS-REFERENCE TO RELATED APPLICATION

This application is a continuation of U.S. Ser. No. 10/465,109 filed on Jun. 19, 2003, now U.S. Pat. No. 7,107,986 which is a continuation of U.S. Ser. No. 10/224,000 filed on Aug. 20, 2002, now issued U.S. Pat. No. 6,601,582, which is a continuation of U.S. Ser. No. 09/445,658 filed on Mar. 31, 2000, now issued U.S. Pat. No. 6,474,331, which was filed pursuant to 35 U.S.C. 371 as a U.S. National Phase Application of International Application No. PCT/EP98/03379 filed on Jun. 8, 1998 claiming priority from GB9711889.7 filed Jun. 10, 1997 and GB9721875.4 filed on Oct. 16, 1997.

FIELD OF INVENTION

The present invention relates to a dispenser having an actuation indicating device for indicating the number of actuations thereof. In particular, the invention relates to metered dose inhalers by means of which medicaments contained in an aerosol container may be administered to a patient.

BACKGROUND OF INVENTION

It is well known to treat patients with medicaments contained in an aerosol, for example, in bronchodilator therapy. It is also known to use for such therapy, medicaments which are contained in an aerosol and are administered to a patient by means of an inhalation device comprising a tubular housing or sleeve in which the aerosol container is located and an outlet tube leading out of the tubular housing. The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the housing is then held by the patient in a more or less upright condition and the mouthpiece or nozzle of the inhalation device is placed in the mouth or nose of the patient. The aerosol container is pressed towards the support to dispense a dose of medicament form the container which is then inhaled by the patient.

A problem arising from use of such known devices is that the patient cannot determine the amount of medicament in the container at any given time. In an extreme case this could mean that the patient, possibly suffering from severe bronchospasm and needing a dose of medicament, will find that the container will not dispense a dose because its contents have already been exhausted.

In solution to the above described problem there has been suggested the use of dose indicating devices, which typically count the number of doses delivered from or remaining in the aerosol container, thereby enabling the patient to determine how much medicament is available in the container for future use. Typically, the dose indicating device has an indexing (i.e. counting) mechanism actuated by movement of the container relative to the housing, wherein a preset amount of relative movement results in a count being indexed.

U.S. Pat. No. 4,817,822 describes an aerosol dispenser having a dose indicating device which, in a first embodiment is removably attached to the end of the protruding portion of the aerosol container. The operating mechanism of the dose counter is located within a housing which extends from the end of the aerosol container along the external surface of the tubular housing.

U.S. Pat. No. 4,817,822 describes a dispenser having a dose indicating device in which the operating mechanism of the dose indicating device is located within a compartment in the housing and is actuated by means of an actuator member attached to the aerosol container.

WO96/16686 describes an aerosol dispenser wherein the operating mechanism of the dose indicating device is electronic and wherein the actuating member comprises a microswitch set into the wall of the housing. The electronic counting mechanism and microswitch are contained within a hermetically sealed enclosure.

U.S. Pat. No. 5,482,030 describes an aerosol dispenser having a mechanical dose indicator device located in and connected to the housing in the vicinity of the outlet tube of the aerosol container when fitted.

Many different pharmaceutical products are sold in the form of aerosol containers requiring different sized container bodies and/or valves according to the required specifications. It is therefore normal for there to be dimensional variations between different aerosol containers. Even between the same products there can be dimensional variations due to manufacturing tolerances.

A problem which is common to all of the dose indicating devices discussed above is that the indexing mechanism, which is actuated by relative movement between the container body and housing, lacks any means of compensating for different pre-actuation positionings of the indexing mechanism relative to the container arising from, for example, dimensional variations between different aerosol containers. Hence, the indexing mechanisms must be dimensioned according to the product with which they are to be used, and so will not be interchangeable with other products. Furthermore, in order for the indexing mechanism to record a count accurately the dimensions of the components of any particular device must be manufactured to the required high tolerances.

SUMMARY OF THE INVENTION

The Applicants have now found that this problem can be ameliorated by use of a coupling mechanism to compensate for the different relative positions of the container and the indexing mechanism. The coupling mechanism acts such as to couple the container to the indexing mechanism. In one aspect, the coupling acts such as to couple the indexing mechanism to the rest position of the container. In another, clearly related aspect, the coupling mechanism acts such as to couple the container to a start index (i.e. start count) position of the indexing mechanism.

According to one aspect of the present invention there is provided a dispenser comprising a housing having a support; a container, insertable within said housing, having an outlet, wherein said container dispenses through said outlet in response to movement of the container relative to the housing; and an actuation indicator having an indexing mechanism actuatable by movement from a rest position of the container relative to the housing; and a coupling mechanism which acts such as to couple the indexing mechanism to said rest position.

Suitably, said coupling mechanism acts to position the indexing mechanism at a start index position when the container is at the rest position.

In one aspect, the coupling mechanism acts to position the indexing mechanism at a zero position on insertion of the container into said housing.

In another aspect, the coupling mechanism acts to position the indexing mechanism at a zero position in response to an initial ('priming') movement of the container from the rest position.

According to another aspect of the present invention there is provided a dispenser comprising a housing having a support; a container, insertable within said housing, having an outlet, wherein said container dispenses through said outlet in response to movement of the container relative to the housing; and an actuation indicator having an indexing mechanism actuatable from a start index position by movement of the container relative to the housing; and a coupling mechanism which acts such as to couple the container to said start index position.

By use of a coupling mechanism it is possible to create an actuation indicator of one size which can be used in dispensers having valves and actuators made within a wide range of manufacturing tolerances and can even fit a range of valves and actuators made to different dimensions.

Suitably, the indexing mechanism is actuatable by a predetermined movement of the container relative to the housing.

Suitably, the indexing mechanism indexes actuation by means of a predetermined rotary movement of a first member driven by movement relative to a second member during actuation of the dispenser. Preferably, the second member remains stationary relative to the housing during actuation of the dispenser.

In one preferred aspect, the first member comprises a pinion carried by a shaft through the coupling mechanism and the second member comprises a rack.

In another preferred aspect, the first member comprises a yoke for engagement with the second member through the coupling mechanism.

Suitably, the coupling element comprises a friction drive mechanism.

Suitably, the container is an aerosol container.

Suitably, the container provides measured doses. Preferably, the actuation indicator indicates the number of doses dispensed from or remaining in the container.

Suitably, the dispenser herein comprises a housing having a support; a container, locatable within said housing, having an outlet member, wherein said container is movable relative to the housing to enable dispensing therefrom and said outlet member is connectable with said support to prevent relative movement therebetween; and an actuation indicator, locatable within said housing. Preferably, the container and actuation indicator are reversably removable from the housing as a single unit.

Suitably, the actuation indicator is engagable with the container in the vicinity of the outlet member. More preferably, the actuation indicator is engagable with the outlet member.

Suitably, the actuation indicator is provided with a grip member which is engagable with a neck portion of the container. Preferably, the neck portion is adjacent to or on the outlet member.

Suitably, the housing is provided with an outlet, more preferably in the form of a mouthpiece. Preferably, the dispenser comprises a passage through which dispensed doses may pass from the container to the outlet.

Suitably, the dispenser is a breath operated inhaler which is actuable in response to the inward breath of a user.

Preferably, the dispenser herein is an aerosol dispenser comprising a housing in which a container is removably located, an outlet leading from the housing and a support in the housing arranged to receive an outlet member of the container and having a passage through which the contents of the container may pass to the outlet, the outlet member being held stationary in the housing support and the body of the container being moveable relative to the outlet and housing to dispense its contents in measured doses, and an actuation indicating device having an actuation indicator for indicating the number of doses dispensed from or remaining in the container. More preferably, the actuation indicating device is tightly connected to the container in the vicinity of the outlet member, such that the container and actuation indicating device may be removed from the housing as a single unit.

Preferably, the dispenser herein is a metered dose inhaler comprising a housing in which the container is removably located, an outlet leading from the housing, a support in the housing arranged to receive the outlet member of the container and having a passage through which the contents of the container may pass to the outlet, the outlet member being held stationary in the housing support and the body of the container being movable relative to the outlet and housing to dispense its contents in measured doses, and a window through which the actuation indicator may be viewed.

BRIEF DESCRIPTION OF THE DRAWINGS

A dispenser according to the invention will now be described with reference to the accompanying drawings in which.

DETAILED DESCRIPTION OF THE PREFERRED EMBODIMENTS

Figure 1:
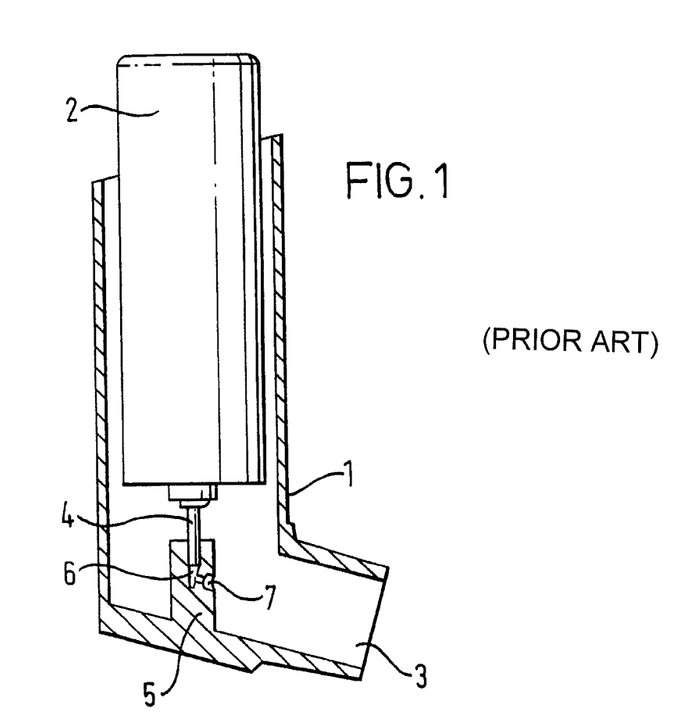
FIG. 1 is a section through a standard inhalation device comprising an aerosol dispenser.

A standard metered dose inhaler shown in FIG. 1 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril.

The aerosol container 2 has an outlet valve stem 4 at one end. This valve member can be depressed to release a measured dose from the aerosol container or, alternatively, the valve stem 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the container 2 spaced from the internal surface of the housing 1. A support 5 is provided at the lower end of the housing 1 and has a passage 6 in which the valve stem 4 of the aerosol container 2 can be located and supported. A second passage 7 is provided in the support 5 and is directed towards the interior of the outlet 3. Thus, when the parts are in the positions shown in FIG. 1, the protruding portion of the aerosol container 2 can be depressed to move the container relative to the valve stem 4 to open the valve and a dose of medicament contained in the aerosol will be discharged through the passage 7 and into the outlet 3 from which it can be inhaled by a patient. One dose will be released from the aerosol container each time it is fully depressed.

Figure 2:
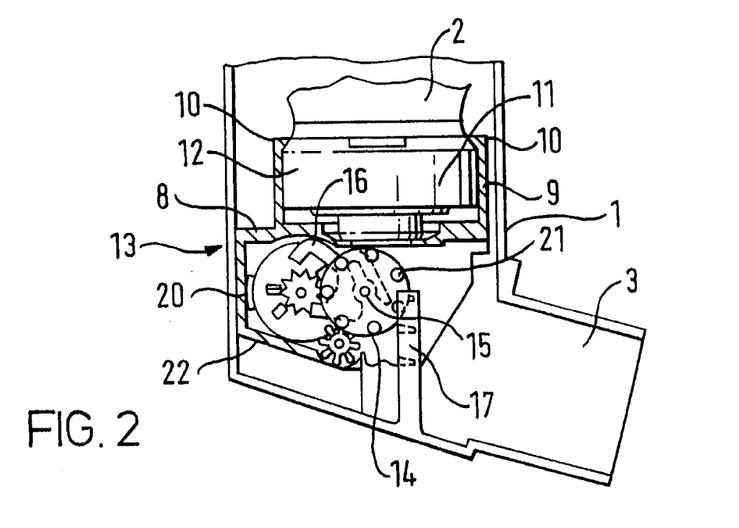
FIG. 2 is a section through the dose indicating device as fitted to an aerosol dispenser in an inhalation device.

FIG. 2 shows the lower part of a device similar to that of FIG. 1 but incorporating a dose indicating device according to the invention. The dose indicating device comprises a body 8 firmly attached to the aerosol container by means of tubular portion 9 formed with grips 10. Tubular portion 9 tightly engages the periphery of valve ferrule 11 which a grip in the form of lip 10 engages around neck 12 of valve ferrule 11 which is formed during assembly when valve ferrule 11 is crimped onto aerosol container 2. Thus the tubular portion 9 and lip 10 form a tight connection to the aerosol container which once assembled by pushing the tubular portion 9 over the valve ferrule 11 cannot easily be dissembled.

Below tubular portion 9, body 8 forms a cradle 22 for mounting counter mechanism 13 and drive pinion 14. Drive pinion 14 is friction mounted on counter mechanism drive shaft 15. Drive pinion 14 is formed with a number of teeth or pegs 21 which can engage with a number of recesses or grooves formed on post 17 in the form of a rack moulded inside housing 1 and extending from the base of the housing 1 parallel to valve stem 4.

Figure 3:
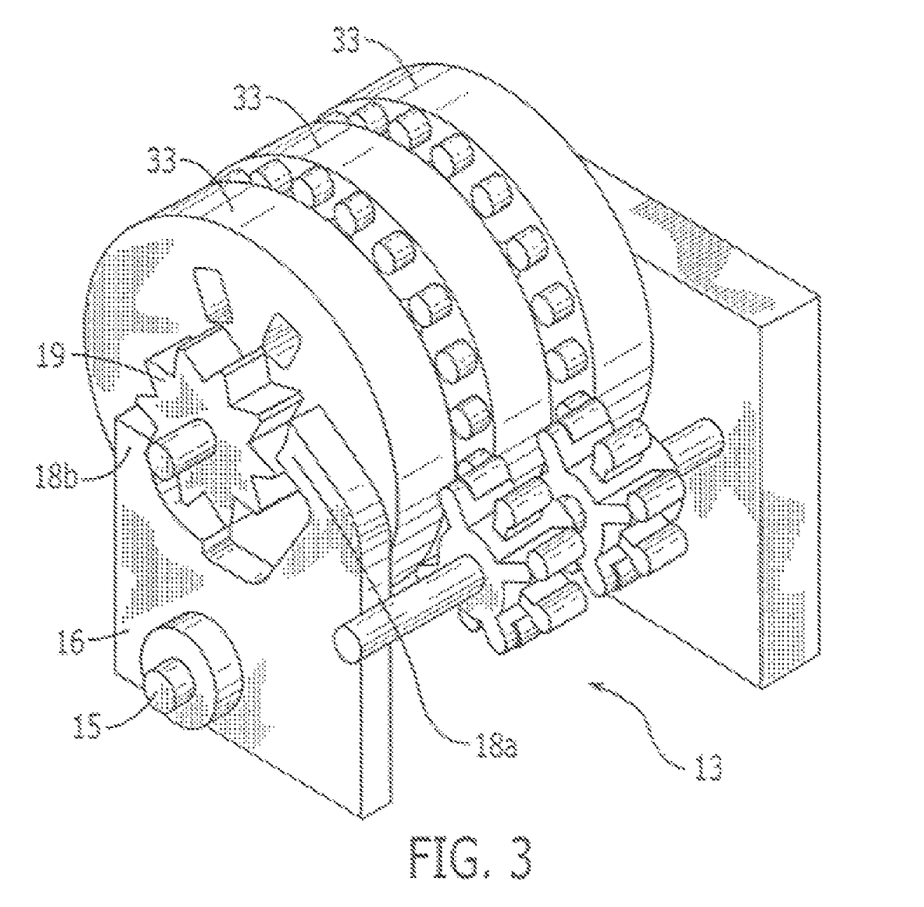
FIG. 3 is a perspective view of a counting mechanism used in the dose indicating device of FIG. 2.

As shown in FIGS. 3 and 4, drive shaft 15 is connected to driver yoke 16 of counter mechanism 13. Driver yoke 16 has two switching latches 18a and 18b spaced either side of star wheel 19 such that driver yoke 16 may tilt about the axis of drive shaft 15 between a first position shown in FIG. 4b in which switching latch 18a engages one side of star wheel 19, and a second position shown in FIG. 4d in which switching latch 18b engages the other side of star wheel 19. Star wheel 19 is connected through a mechanism, similar to that described with reference to reference numerals 2 to 8 in FIGS. 1 to 3 of European Patent No. 0280104, to three digit wheels 33, which have numbers printed on their circumferential faces as described below. When located in the housing 1, counter mechanism 13 is small enough to be located to the sides of and behind support 5 so as not to interfere with the aerosol flume as it emerges from passage 7.

The aerosol container 2 may be supplied to the patient with the dose indicating device ready assembled thereto. Alternatively, the housing 1 may be supplied to the patient with the dose indicating device located in the position shown in FIG. 2 and the aerosol container 2 supplied separately. In this case, the patient is instructed to insert the aerosol container 2 into the housing 1 with the valve stem first. Upon first insertion of the container into the housing, the tubular portion 9 and lip 10 of the dose indicating device ride over the periphery of valve ferrule 11 of the aerosol container 2 until lip 10 snaps around neck 12. Thereafter, the dose indicating device is attached to the aerosol container 2.

Other means of attachment of the dose indicator to the container are envisaged including adhesive attachment; use of welded shrink sleeves; heat forming; crimping; ultrasonic welding; and by the present of an o-ring elastomer on the container which is fixedly piercable by barbs on the attachment member of the dose indicator.

To actuate the device, the protruding portion of the aerosol container is depressed as described above with reference to FIG. 1. As the aerosol container carrying the dose indicating mechanism moves within housing 1, drive pinion 14 starts to turn, through its engagement with post 17, causing rotation of drive shaft 15 and driver yoke 16. As driver yoke 16 tilts with rotation of drive shaft 15 switching latch 18a moves into engagement with star wheel 19 (FIG. 4a) causing an incremental anti-clockwise rotation of a half tooth pitch of the star wheel until the switching latch 18a can move no further in this direction, the switching latch being positioned between two adjacent teeth of the star wheel FIG. 4b). At this point, drive shaft 15 cannot rotate any further and any further movement of the aerosol container into housing 1 results in drive pinion 14 continuing to rotate through its engagement with post 17 by virtue of the friction coupling between pinion 14 and drive shaft 15.

Figure 4A:
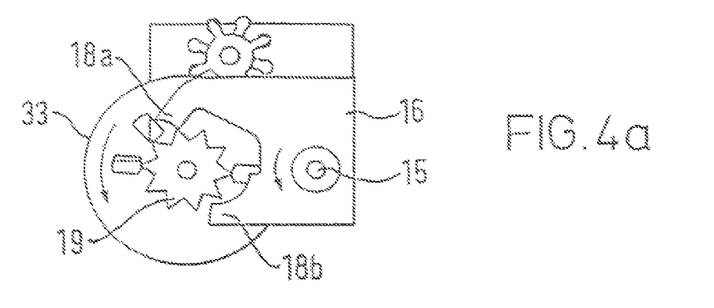
FIGS. 4*a*, 4*b*, 4*c*, and 4*d* show the sequence of operation of the counter mechanism of FIG. 3.
Figure 4B:
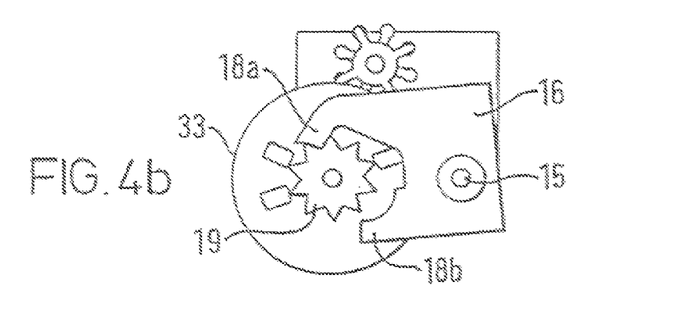
Figure 4C:
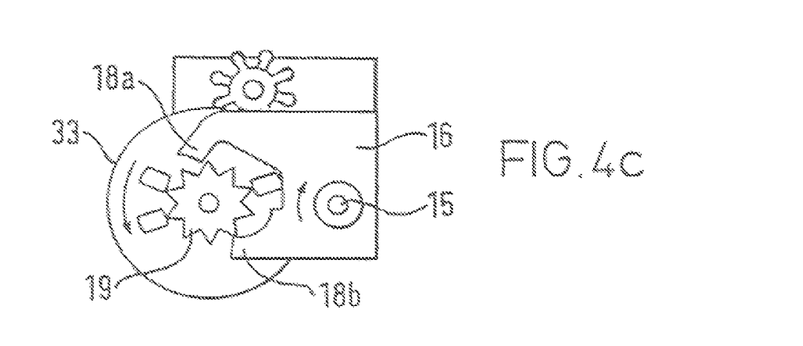
Figure 4D:
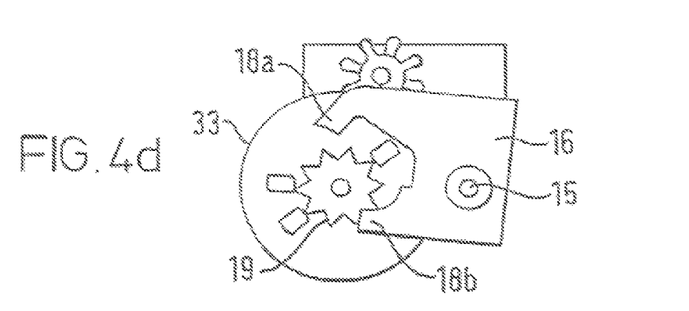

When the valve stem 4 has reached its fully depressed position and a metered dose of medicament has been discharged from the aerosol container, the aerosol container is allowed to return to its original position. As the aerosol container and dose indicating mechanism return to their original position, drive pinion 14 starts to rotate in the opposite direction together with drive shaft 15 and driver yoke 16. Thus, driver yoke 16 tilts such that switching latch 18a moves out of engagement with star wheel 19 while switching latch 18b moves into engagement therewith (FIG. 4c), causing further incremental anti-clockwise rotation of a half tooth pitch of the star wheel until switching latch 18b can move no further in this direction (FIG. 4d). Again, drive shaft 15 cannot rotate any further at this point and any further movement of the aerosol container out of housing 1 results in drive pinion 14 continuing to rotate through its engagement with post 17 by virtue of the friction coupling between pinion 14 and drive shaft 15. In this way it can be seen that the friction coupling acts as a lost motion coupling which allows the dose indicating device to be used with aerosol containers having valves with different lengths of travel of valve stem during actuation.

Each time the aerosol dispenser is actuated the star wheel is made to rotate through two incremental anti-clockwise movements as described above. These movements are translated through the counter mechanism into appropriate movements of the digit wheels 33, one number on each of the printed circumferential faces of the digit wheels being clearly visible through the window 20 at the back of the housing 1 (as shown in FIG. 2), to indicate that a further dose of medicament has been dispensed. By having three digit wheels 33 it is possible for the dose counter to be used to count hundreds of doses. Clearly if fewer than one hundred doses are to be contained within the dispenser, the dose counter could comprise fewer digit wheels. Alternatively, if a thousand or more doses are to be contained, then one or more additional digit wheels could be added as appropriate.

To remove the aerosol container 2 from the housing for cleaning, the aerosol container 2 may be withdrawn from the housing 1 in the usual manner. As the container is withdrawn, the friction coupling between drive pinion 14 and drive shaft 15 allows such further movement as is required for the drive pinion to come out of engagement with the post 17 without causing any further indexing of the counter mechanism. Once removed, the housing 1 may be cleaned as described without fear of interfering with or damaging the dose indicating device, which remains firmly connected to the aerosol container 2.

When the housing 1 is clean, the aerosol container 2 with dose indicating device may be re-inserted into the housing 1. During insertion, drive pinion 14 will engage post 17 and start to rotate until the aerosol container reaches its normal rest position with the valve stem 4 located in support 5. As the drive pinion 14 rotates, the friction coupling will act as a lost motion mechanism as described above, allowing for any travel of the aerosol container as between first engagement of drive pinion 14 and post 17, and location of valve stem 14 in support 5. In this way, the friction coupling automatically accommodates and compensates for different lengths of valve stems protruding from the ferrule, which would otherwise result in different relative start positions of the container relative to the indexing mechanism.

Figure 5A:
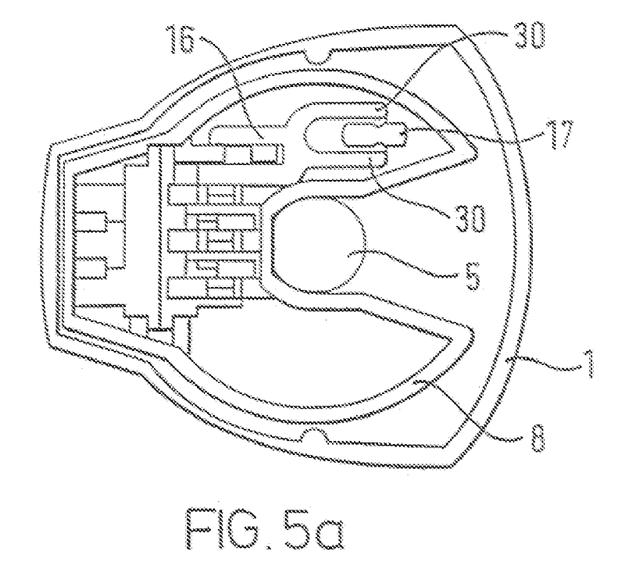
FIGS. 5*a* and 5*b* show a lateral and a longitudinal section through a second embodiment of the dose indicating device as fitted into the housing of an inhalation device.
Figure 5B:
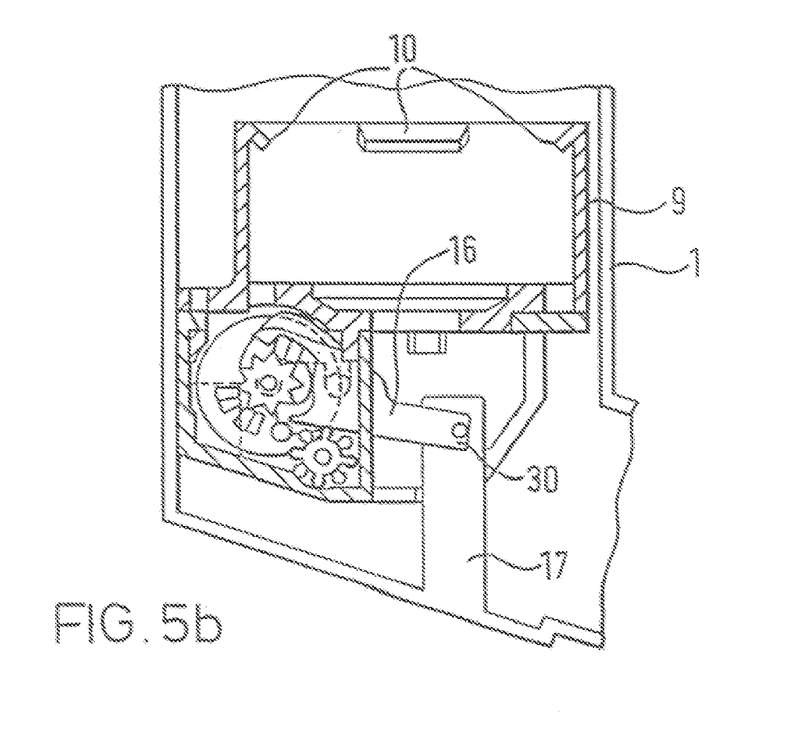
Figure 6:
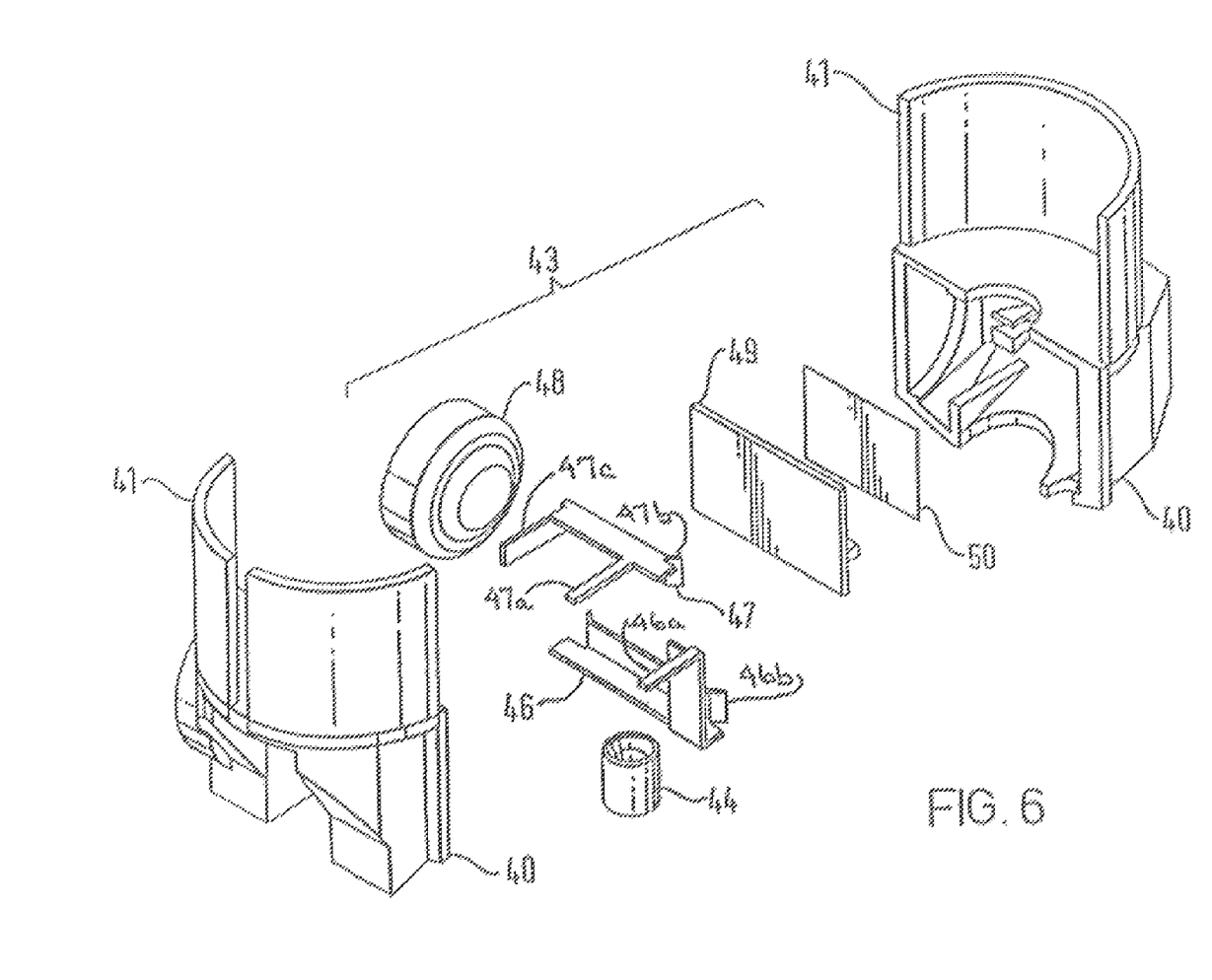
FIG. 6 shows an exploded view of a dose indicating device according to a third embodiment of the invention.
Figure 7:
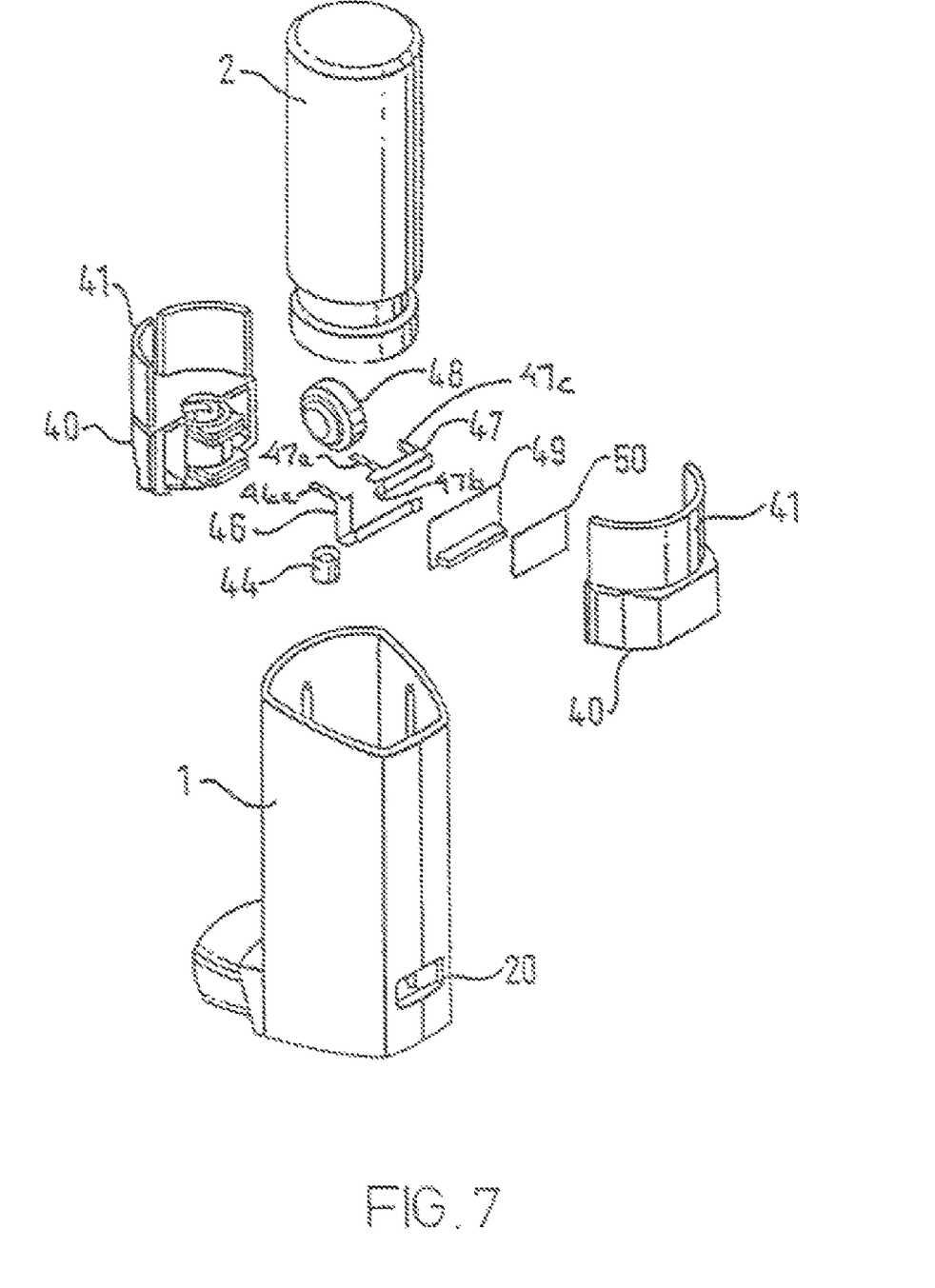
FIG. 7 shows another exploded view of the dose indicating device of FIG. 6 together with an aerosol container and housing.

FIG. 5 shows an alternative lost motion coupling mechanism which may be used in an aerosol dispenser according to the invention. In this embodiment, instead of a pinion, driver yoke 16 is formed with two resilient arms 30 between which post 17 is grippingly engaged (FIG. 5a). Post 17 is formed with ribs on its surface (not shown) which provide a rough surface finish to create the level of friction required between arms 30 and post 17 such that arms 30 will grip post 17 until the load applied overcomes the friction.

Upon actuation of the device, as the aerosol container and dose indicating mechanism move, the friction engagement between arms 30 and post 17 cause driver yoke 16 to tilt about the axis of shaft 15 (not shown in FIG. 5), so moving switching latch 18a into engagement with star wheel 19 as discussed in relation to the first embodiment. As switching latch 18a reaches its limit of travel, driver yoke 16 can move no further, and any further movement of the aerosol container into housing 1 results in arms 30 slipping down post 17 by virtue of the friction coupling. Upon return to its original position, driver yoke 16 tilts in the other direction until switching latch 18b moves into engagement with star wheel 19 and can move no further. Any further movement of the aerosol container out of housing 1 results in arms 30 slipping up post 17.

FIGS. 6 to 9 show an inhalation device fitted with an electro-mechanical dose indicating device according to the invention. As with the mechanical embodiments discussed above, the dose indicating device comprises a body 40 firmly attached to the aerosol container by means of tubular portion 41 formed with grips (not shown). Tubular portion 41 tightly engages the periphery of valve ferrule 11 while a grip in the form of a lip engages around neck 12 of valve ferrule 11. Thus the tubular portion 41 and lip form a tight connection to the aerosol container which once assembled by pushing the tubular portion 41 over the valve ferrule 11 cannot easily be disassembled.

Below tubular portion 41, body 40 forms a cradle for mounting counter mechanism 43, and defines a chamber for accommodating switch slide 44. Switch slide 44 is a cylindrical washer made of silicone rubber and having a bore of such a diameter that, with the can and dose indicating device mounted within the actuator housing, it provides a friction fit on pin 45, which is moulded in the housing and protrudes through a hole in body 40. The friction fit of switch slide 44 on pin 45 ensures the switch slide will not move along the pin unless pushed.

Figure 9:
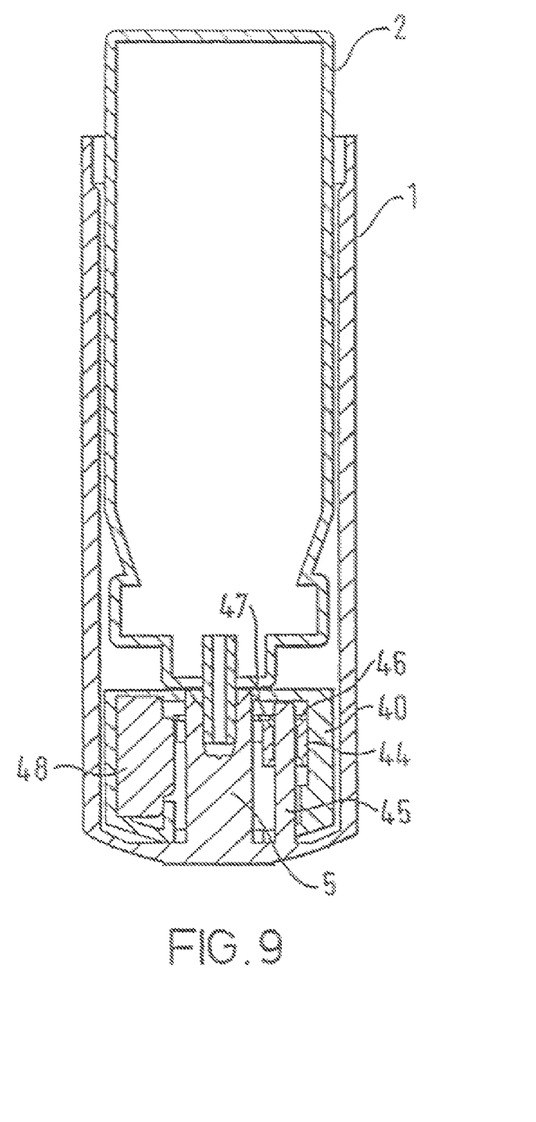
FIG. 9 shows a schematic section through the inhalation device of FIG. 8 in an actuated position.

Two contact members 46, 47, both of which comprise a switch contact and a circuit board contact, and one of which further comprises a battery contact, are mounted such that the battery and circuit board contacts are in constant contact with a first terminal of the battery 48 and printed circuit board (PCB) 49 respectively. The switch contacts do not contact each other but are positioned either side of pin 45, and define the upper limit of movement of the switch slide 44 within its chamber. Thus, when switch slide 44 is in its position as shown in FIG. 9, it makes contact with both switch contacts, so closing the circuit between them due to the electrical conductivity of the silicone rubber of the switch slide. Although in the embodiment described the switch slide is made of silicone rubber, it will be appreciated that it could alternatively be made of a non-conductive rubber having an insert at its upper face made of metal or some other conductive material.

In addition to its connections with contact members 46, 47, PCB 49 also has connections to the other terminal of the battery and to a three digit liquid crystal display (LCD) 50 in a conventional manner. The PCB comprises an application specific integrated circuit (ASIC), which provides the logic by which the dose indicator can be checked, programmed and made operational, as discussed in more detail below, to keep a record of how many times the switch contact circuit is closed and drives the LCD to display the number of doses remaining in the aerosol container. The ASIC is thus designed and programmed accordingly in a known manner.

Instead of a digital display, the LCD could alternatively be formatted to display an analogue indication. When the aerosol container is mounted in the actuator housing, LCD 50 is visible through window 20. In the embodiment depicted in FIG. 7, the LCD and window are located at the back of the housing, but they could equally be located at the front or some other part of the housing.

The Counter mechanism 43 is small enough to be located to the sides of and behind the stem block (support 5) moulded in housing so as not to interfere with the aerosol flume as it emerges.

Figure 8:
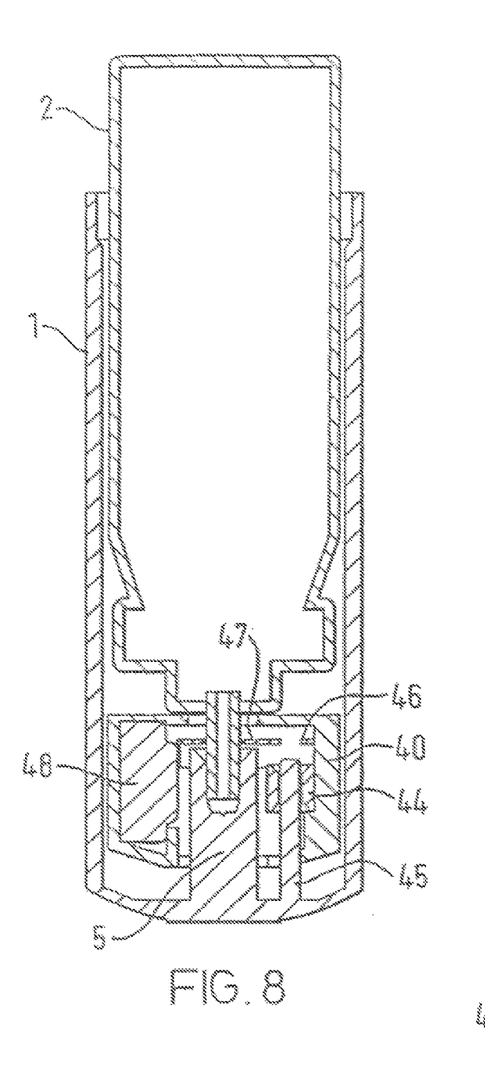
FIG. 8 shows a schematic section through an inhalation device comprising the dose indicating device of FIG. 6 in a rest position.

To actuate the device, the protruding portion of the aerosol container when fitted into the actuator housing is depressed as described above. As the aerosol container carrying the dose indicating mechanism moves within the housing from its rest position (shown in FIG. 8), the chamber accommodating switch slide 44 moves down until the upper face of switch slide 44, which is mounted on pin 45, meets switch contacts 46, 47 and the switch circuit is closed. This causes the ASIC to decrement the number displayed by the LCD 50. As the aerosol container continues to move, a metered dose of medicament is discharged from the valve, while switch slide 44 is pushed down along pin 45 by virtue of the friction fit of the switch slide on the pin until the valve stem reaches its limit of travel and the aerosol container moves no further (FIG. 9). In this way, it can be seen that the friction fit of the switch slide 44 on pin 45 allows for over-travel of the valve stem after the switch circuit has been closed, so acting as a lost motion coupling. The aerosol container is then allowed to return to its original position within the housing, and as it returns, the chamber accommodating switch slide 44 moves up breaking the switch circuit as switch contacts 46, 47 move away from switch slide 44. Body 40 then meets the lower face of switch slide 44 and draws the switch slide up along pin 45 until the valve stem returns to its rest position (FIG. 8).

Because the dose indicating device is designed to be suitable for use in connection with different sized aerosol containers containing different numbers of doses to be delivered, the ASIC is designed to be factory set in accordance with the size of aerosol container with which the dose indicating device is assembled. After assembly of the dose indicating device and first connection of the battery, the ASIC enters a self-test mode. After this, the programming mode may be entered by activating the switch, allowing it to be programmed to count down from the appropriate number of doses (e.g. 200, 120, 80 or 60). This may be done automatically on a packing line. After programming has taken place, the ASIC enters the counting mode, where the LCD decrements upon closing of the switch contact circuit. When the count of zero is reached, the ASIC is designed to prevent the count from decrementing any further in a known manner. In order to prevent spurious readings due to the effects of switch 'bounce', the ASIC may be designed to decrement only after the switch circuit has been closed for a predetermined length of time in a known manner. In the event of the aerosol container getting jammed in the actuated position after operation, or the switch circuit jamming closed due to mechanical damage or contamination, the ASIC may be designed to blank the LCD to alert the user that there is a problem.

As with the other embodiments of the invention described above, the aerosol container may be withdrawn from the actuator housing in the usual manner. As the container is withdrawn, body 40 draws the switch slide up along pin 45 until it clears the pin altogether. Once removed, the housing may be cleaned without interfering with or damaging the dose indicating device, which remains firmly connected to the aerosol container.

During re-insertion of the aerosol container, which can only occur when the body of the dose indicating device is correctly orientated with respect to the housing by virtue of their respective shapes, switch slide 44 engages and is pushed up by pin 45 until the upper face meets the switch contacts. Further insertion of the aerosol container results in switch slide 44 being pushed down along pin 45 until the valve stem is seated back within support 5.

It will be appreciated that by programming of the ASIC, one design of dose indicating device could be used in conjunction with a range of aerosol containers of various capacities. By virtue of the switch mechanism, the same design of dose indicating device can also be used in conjunction with a range of different valves having different lengths of valve stem and different stem travel specifications.

Whilst the present invention has been described in detail in respect of a metered dose inhaler actuatable manually by the patient it will be appreciated that other actuation mechanisms can be substituted. In particular, the use of a breath operated inhaler in which the actuation is assisted, and is responsive to, preferably triggered by, the inward breath of the patient, is also envisaged.

The dispenser of the invention is suitable for dispensing medicament, particularly for the treatment of respiratory disorders. Appropriate medicaments may thus be selected from, for example, analgesics, e.g., codeine, dihydromorphine, ergotamine, fenfanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

That which is claimed:

1. An aerosol container unit adapted for location in a housing of a metered dose inhaler (MDI) comprising a support and an outlet selected from a mouthpiece and a nasal nozzle, the aerosol container unit having:

an aerosol container for containing a number of metered doses of a pharmaceutical inhalation formulation, the container having a first end from which an outlet valve stem protrudes along an axis along which axis the stem is able to be repeatedly depressed into the container for dispensing said metered doses of the formulation from the container when present therein, and a dose indicating device for indicating the number of metered doses which:

(i) are dispensed from the container, or (ii) remain in the container, wherein the dose indicating device has a body which is fixedly mounted to the first end of the aerosol container so that the body and the container are fixed against axially relative movement, and the first end of the aerosol container is inserted into an open end of the body, wherein the unit is locatable in an operational position in said MDI housing with the outlet valve stem in the MDI housing support, and wherein when the unit is in the operational position the container and the dose indicating device body are movable axially, in an axially fixed relationship, relative to the outlet valve stem and the MDI housing support to cause the outlet valve stem to be depressed into the container so that a metered dose of the formulation, when present, is dispensed through the MDI housing support into the MDI housing outlet for delivery to a patient.

2. The unit of claim 1, wherein dose indicating device is a dose counter.

3. The unit of claim 2, wherein the dose counter has a counting mechanism which includes a plurality of coaxially mounted count wheels, the count wheels being provided with a sequence of numbers on the circumferences thereof for representing the number of metered doses (i) dispensed from the container, or (ii) remaining in the container.

4. The unit of claim 1, wherein the dose indicating device body has a tubular housing having the open end into which the first end of the aerosol container is inserted.

5. The unit of claim 1, wherein the dose indicating device is attached to the aerosol container at a neck thereof located at the first end.

6. The unit of claim 5, wherein the neck is formed by a valve ferrule.

7. A metered dose inhaler (MDI) comprising:
an aerosol container unit as claimed in claim 1, and
a said housing.

* * * * *